(12) United States Patent
Mroncz et al.

(10) Patent No.: US 7,766,901 B2
(45) Date of Patent: Aug. 3, 2010

(54) DEVICE FOR TREATING BLADDER-EMPTYING DYSFUNCTIONS OF A HUMAN

(75) Inventors: Andreas Mroncz, Sindelfingen (DE); Gabriele Wohnhas, Bergrheinfeld (DE)

(73) Assignee: Medi-Globe GmbH, Rohrdorf-Achenmuehle (DE)

( * ) Notice: Subject to any disclaimer, the term of this patent is extended or adjusted under 35 U.S.C. 154(b) by 1062 days.

(21) Appl. No.: 10/585,361

(22) PCT Filed: Jan. 12, 2005

(86) PCT No.: PCT/DE2005/000029
§ 371 (c)(1),
(2), (4) Date: Jul. 6, 2006

(87) PCT Pub. No.: WO2005/065758
PCT Pub. Date: Jul. 21, 2005

(65) Prior Publication Data
US 2009/0192451 A1 Jul. 30, 2009

(30) Foreign Application Priority Data
Jan. 12, 2004 (DE) .................. 10 2004 001 670

(51) Int. Cl.
*A61M 27/00* (2006.01)
(52) U.S. Cl. ............... 604/544; 604/8; 604/9; 604/249; 604/288.03; 604/537; 604/540; 600/29; 600/30; 600/31; 623/64; 623/23.65; 623/23.68; 623/23.7; 137/854; 137/315.24; 251/247
(58) Field of Classification Search .......... 604/8, 604/9, 249, 288.03, 537, 540, 544
See application file for complete search history.

(56) References Cited

U.S. PATENT DOCUMENTS 4,026,298 A  5/1977  Grausz (Continued)

FOREIGN PATENT DOCUMENTS

DE  33 21 877  12/1984

(Continued)

OTHER PUBLICATIONS

International Search Report in English, Jul. 2006.

*Primary Examiner*—Tatyana Zalukaeva
*Assistant Examiner*—Ilya Y Treyger
(74) *Attorney, Agent, or Firm*—Collard & Roe, P.C.

(57) ABSTRACT

The invention relates to a device for treating bladder emptying dysfunctions of a human, in which a catheter that can be inserted into the urethra is provided with a bladder emptying channel and with a balloon arrangement, which serves to seal the bladder and to hold the catheter inside the bladder lumen and which can be filled with a fluid. In addition, an automatically closing valve having an elastically held closure part is provided in a proximal end area of the catheter and is connected via a connecting channel filled with an actuating fluid to an actuating balloon placed at the distal end section of the catheter. Without the use of mechanical means, the closure part can be lead out of a sealing system solely due to a hydraulic action effected by the actuating balloon via the hydraulic pressure built up in the connecting channel at said proximal end section. This closure part can be lead out of the sealing system to such an extent as to open the bladder emptying channel of the catheter for an unobstructed passage of urine.

14 Claims, 3 Drawing Sheets

U.S. PATENT DOCUMENTS

| | | |
|---|---|---|
| 4,249,536 A | 2/1981 | Vega |
| 4,932,938 A | 6/1990 | Goldberg et al. |
| 5,378,238 A * | 1/1995 | Peters et al. ............ 604/99.04 |
| 5,762,996 A * | 6/1998 | Lucas et al. .................. 427/2.3 |
| 5,989,288 A * | 11/1999 | Pintauro et al. ............... 600/30 |
| 6,090,083 A * | 7/2000 | Sell et al. .................... 604/249 |
| 6,119,697 A | 9/2000 | Engel et al. |
| 6,167,886 B1 | 1/2001 | Engel et al. |
| 6,355,014 B1 * | 3/2002 | Zadno-Azizi et al. .... 604/99.02 |
| 6,855,126 B2 * | 2/2005 | Flinchbaugh ............... 604/106 |
| 2004/0236365 A1 * | 11/2004 | Cioanta et al. .............. 606/191 |

FOREIGN PATENT DOCUMENTS

| | | |
|---|---|---|
| DE | 40 14 369 | 11/1990 |
| DE | 19621420 | 12/1997 |

* cited by examiner

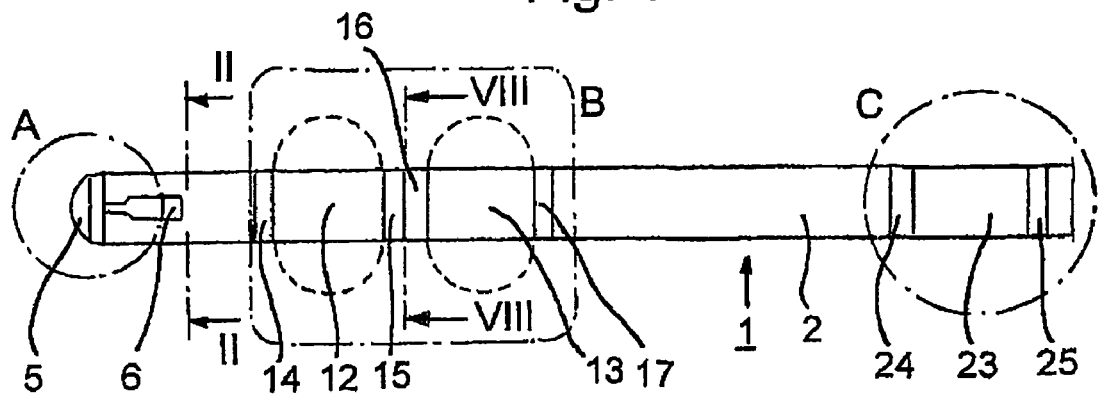
Fig. 1
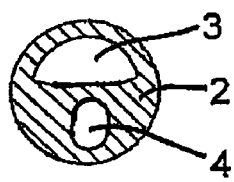
Section II-II
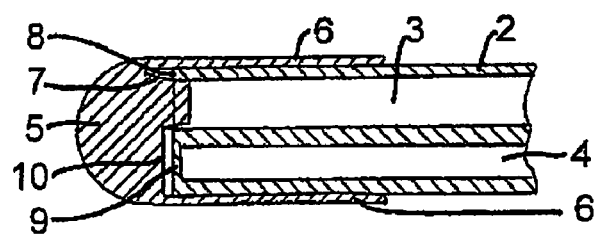
Detail A in section
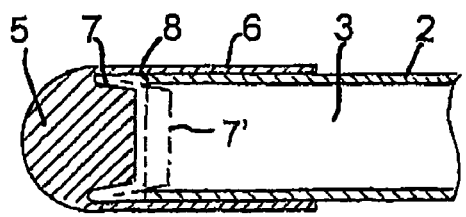
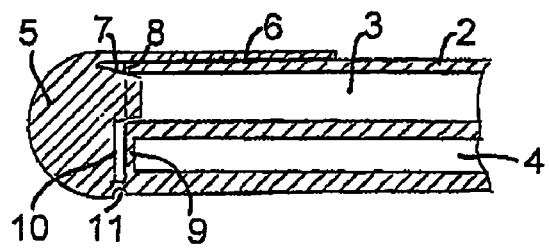

Detail B in section

Section VIII-VIII

Detail C in section

Detail D in section

DEVICE FOR TREATING BLADDER-EMPTYING DYSFUNCTIONS OF A HUMAN

CROSS REFERENCE TO RELATED APPLICATIONS

Applicants claim priority under 35 U.S.C. §119 of German Application No. 10 2004 001 670.4 filed Jan. 12, 2004. Applicants also claim priority under 35 U.S.C. §365 of PCT/DE2005/000029 filed Jan. 12, 2005. The international application under PCT article 21(2) was not published in English.

The invention relates to a device for treating bladder-emptying dysfunctions of a human, having a catheter that can be introduced into the urethra, which catheter has a urine-emptying channel and carries a balloon arrangement that can be filled with a fluid, to seal the bladder and to hold the catheter in the bladder lumen, which arrangement can be filled with or emptied of the said fluid by means of at least one channel that runs along the catheter wall and is sealed off at the distal end segment of the catheter, and having an automatically closing valve accommodated in a proximal end segment of the catheter, whereby the length of the catheter is dimensioned in such a manner that its distal end lies within the urethra in the inserted state, and the proximal end segment in question carries a hydraulic activation mechanism for opening the valve, whereby the activation mechanism can be hydraulically impacted by means of mechanical pressure on the activation balloon that is disposed on the distal end segment of the catheter, filled with activation fluid, and connected with the activation mechanism by way of a connection channel.

A device of the type stated above is already known (DE 196 21 420 C2). It has now turned out in practice that in the case of the known device in question, a relatively great mechanical pressure must be exerted in order to open the automatically closing valve provided at the proximal end of the device. However, the exertion of such a high mechanical pressure is perceived by the patient in whom the device as a whole is being used as being uncomfortable, with the consequence that the acceptance of the use of the known device in question is not particularly great.

It is therefore the task of the invention to further develop a device of the type stated initially, in such a manner that the valve provided at the proximal end of the device can be opened at a lower mechanical activation pressure than in the case of the known device, so that the acceptance of the use of the device developed further in this manner can be increased.

This task is accomplished, in the case of a device of the type stated initially, according to the invention, in that the said activation mechanism is formed in that the valve contains a closure part elastically connected with the said proximal end segment of the catheter in such a manner that this part seals off the catheter at the said proximal end segment in the non-activated state of the activation balloon, and that the closure part in question can be moved out from the sealing contact solely in response to a hydraulic impact by means of the activation balloon, by means of the effective hydraulic pressure built up thereby at the said proximal end segment, to such an extent that the urine-emptying channel of the catheter is opened for unhindered passage of urine.

The invention is characterized by the advantage of an activation mechanism for the said valve that has a relatively simple design, and makes do with a relatively low mechanical pressure to open the closure part provided at the proximal end segment of the catheter for unhindered passage of urine. The design principle used for this purpose in the present invention is significantly simpler than the design principle for valve opening and closing proposed in the case of the known device mentioned above, according to which an activation mechanism having a bendably elastic spring rod is used, among other things. Therefore the use of the device according to the invention should find better acceptance than the previously known device.

Preferably, the valve closure part having a conically shaped contact surface makes it possible to seal off the urine-emptying channel of the catheter at an end edge at the proximal catheter end. This measure brings with it the advantage of a particularly effective seal of the urine-emptying channel.

It is practical if the closure part and the proximal end segment of the catheter are elastically connected with one another by means of holder elements. This brings with it the advantage of a particularly simple configuration of the closure part and the catheter.

According to another practical further development of the present invention, the closure part is connected with the proximal end segment of the catheter by means of a joint element as well as by means of at least one elastic holder element. In this connection, secured positioning of the closure part on the catheter is made possible by means of the use of the aforementioned joint element.

A particularly simple possibility, in terms of design, for connecting the closure part and the proximal end segment of the catheter by means of the holder elements results, according to another practical embodiment of the invention, in that the elastic holder element, in each instance, is formed on the closure part or on the proximal end segment of the catheter, and is separately attached to the proximal end of the catheter or to the closure part, respectively, with its other end, in each instance.

A particularly simple attachment of the aforementioned other end of each holder element, in each instance, results, in practical manner, in that it is attached, with the other end in question, to the proximal end of the catheter or to the closure part, respectively, by means of a glued connection.

It is particularly advantageous if, according to another practical embodiment of the present invention, the connection channel connected with the activation balloon contains a pressure lumen separated by a separate valve in the region of the proximal end segment of the catheter, and when this lumen is filled with the activation fluid, by means of activation of the said activation balloon, the closure part can be lifted up from its sealing contact on the said urine-emptying channel of the catheter. The pressure lumen in question is essentially pumped up with activation fluid, by means of activation of the activation balloon, similar to how a bicycle tube is pumped up, for example. In other words, a hydraulic pressure reinforcement essentially takes place here. As a result, it is possible to make do with a particularly low mechanical activation force in the region of the activation balloon, and nevertheless make available a hydraulic pressure of the activation fluid in the aforementioned separate pressure lumen that results in opening of the aforementioned closure part.

In order to open the closure part only during a limited time span in connection with the practical further development considered above, the said valve is configured in such a manner, according to a further practical embodiment of the present invention, that it allows in-flow of the activation fluid into the said pressure lumen at a first, relatively high velocity, and permits back-flow of the activation fluid in question from the said pressure lumen at a significantly lower second velocity, in comparison. This results, in advantageous manner, in a particularly slight effort, in terms of design, in order to achieve time-limited opening of the aforementioned closure part.

It is advantageous, in connection with the practical further development of the present invention discussed above, if the valve that separates the pressure lumen from the activation balloon has a valve shaft that has a passage opening in the pressure lumen that is accessible from the activation balloon, which opening is surrounded by a valve tube. In principle, such a valve corresponds to a known bicycle tube valve. In this connection, in order to limit the time during which the said closure part is open, the effect can be utilized that after the aforementioned pressure lumen has been "pumped up," the activation fluid situated in it tries to escape between the valve shaft and the valve tube, and to bring about pressure relief in the pressure lumen in question. In this connection, it has been shown that the length with which the valve tube projects beyond the aforementioned passage opening of the valve shaft is decisive for the dwell time of the activation fluid in the said pressure lumen and therefore for the opening duration of the aforementioned closure part. The shorter the excess length, the shorter the opening time of the aforementioned closure part.

Preferably, the catheter and the closure part consist of silicone, and it is practical if the balloon arrangement and the activation balloon also consist of silicone. In this way, a biocompatible material is used for the elements in question, in each instance.

In the case of the present invention, it is advantageous if oil is used as the activation fluid. In this connection, the use of olive oil has particularly proven itself, since this oil brings absolutely no problems with it when used. This is because, as has been shown, olive oil does not tend to diffuse through the material, in each instance, and particularly through silicone of the catheter, the closure part, the balloon arrangement, and the activation balloon. The reason for this probably lies in the fact, according to present knowledge, that the olive oil molecules are larger than molecules of other oils, and therefore cannot diffuse through the molecular structure of the material being used, in each instance, particularly through the silicone.

The invention will be described in greater detail using exemplary embodiments and drawings.

FIG. 1 shows an embodiment of a device according to the present invention, in an enlarged schematic representation.

FIG. 2 shows an enlarged sectional view along the section line II-II drawn in FIG. 1.

FIG. 3 shows a detail indicated in FIG. 1 as A, in an enlarged sectional view.

FIG. 4 shows the detail A shown in FIG. 3 in another sectional plane.

FIG. 5 shows an alternative implementation of the detail A shown in FIG. 3, in an enlarged sectional view.

Figure 6:
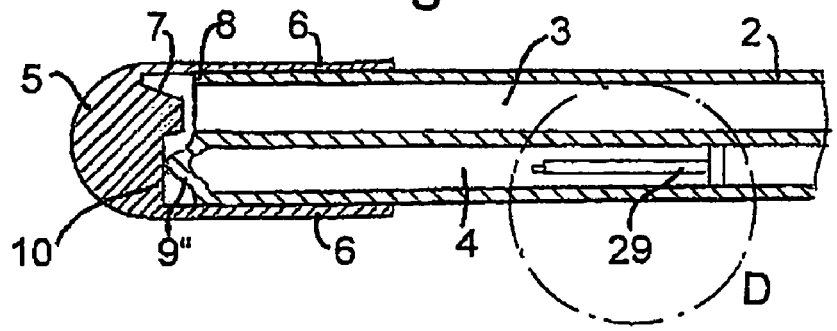
FIG. 6 shows, proceeding from the sectional view shown in FIG. 3, for one thing, the conditions that result when an activation fluid is effective, as well as the formation of a separate pressure lumen in an activation channel.

In FIG. 1, an embodiment of a device 1 according to the present invention is shown in an enlarged schematic representation. The device 1 in question has a catheter 2, which has, among other things, a urine-emptying channel, as will become more clearly evident below, and carries a valve on its proximal end segment, which is shown on the left in FIG. 1, which valve can be used to open and close the urine-emptying channel in question. At this point, it should be noted that when using the device 1, the aforementioned proximal end segment of the catheter 2 lies in the bladder of a human being, in whose urethra the catheter 2 in question is accommodated. Preferably, the catheter and the aforementioned valve consist of biocompatible silicone.

The proximal end segment of the catheter 2, shown on the left in FIG. 1, has a cross-section as shown in FIG. 2, for example, which shows an enlarged sectional view along the section line II-II drawn in FIG. 1. As is evident from FIG. 2, the catheter 2 contains the aforementioned urine-emptying channel 3 and a further activation channel 4, also referred to as a connection channel here, in the proximal end segment in question; an activation fluid is brought to effect in the latter channel, as will be explained in greater detail below. Here, oil, preferably olive oil, is used as the activation fluid. It is true that the urine-emptying channel 3 and the activation channel 4 are shown with oval cross-sections here; however, it should be easily understood that they could also possess different cross-sections.

The valve provided at the aforementioned proximal end segment of the catheter 2 comprises a closure part designated as 5 in FIG. 1. This closure part 5, whose task consists of sealing the urine-emptying channel 3 off at the proximal end segment of the catheter 2 in question, and of opening it for unhindered passage of urine as needed, is elastically connected with the proximal end of the catheter 2 by means of a holder element 6 shown in tab shape in FIG. 1. At this point, it should be noted that a predetermined number, for example three or four holder elements, can be provided of the holder element 6. In this connection, the holder element 6, in each instance, can be connected with the proximal end of the catheter 2 merely with its broad tab part shown in FIG. 1. The thin ridge part of the holder element 6, in each instance, gives this element the elasticity required for closing and opening the valve containing the closure part 5.

In FIG. 3, the detail A present in the region indicated with A in FIG. 1 is shown in an enlarged sectional view. As is evident, the urine-emptying channel 3 and the activation channel 4 are present in the catheter 2. The urine-emptying channel 3 is sealed off from the closure part 5 by means of a contact part 7 having a contact surface that is configured conically, in that the conically configured contact surface in question rests against a proximal end edge 8 of the catheter material that surrounds the urine-emptying channel 3. In this connection, such a seal is more effective than a surface-type seal between the contact surface 7 and a correspondingly configured contact surface on the proximal end of the urine-emptying channel 3.

According to FIG. 3, the closure part 5 is connected with the proximal end segment of the catheter 2 by means of two holder elements 6 which are preferably connected with the outside of the proximal end segment of the catheter 2 in the manner explained in connection with FIG. 1, specifically by means of a glued connection. For this glued connection, a so-called medical adhesive, which is biocompatible, can be used.

From FIG. 3, it is furthermore evident that the activation channel 4 is closed off by means of a closure wall 9 at its proximal end, which wall is shown as having a relatively slight thickness here. This closure wall 9 lies opposite a correspondingly shaped activation surface 10 of the closure part 5. It is true that an interstice is shown between the closure wall 9 and the activation surface 10 in FIG. 3; however, in practice this interstice does not have to be provided.

FIG. 4 illustrates the detail A shown in FIG. 3 when considering merely the urine-emptying channel 3, in section. While FIG. 3 illustrates the conditions that result from a consideration in the vertical sectional direction in the case of the sectional view according to FIG. 2, FIG. 4 shows the conditions that are present according to FIG. 2 in the horizontal sectional direction through the urine-emptying channel 3. According to FIG. 4, the closure part 5 with its conically configured contact part 7 is moved away from the proximal end edge or border 8 of the urine-emptying channel 3 to such an extent that the urine-emptying channel 3 of the catheter 2 is opened for unhindered passage of urine. In this case, the holder elements 6 shown in FIG. 4, which are attached to the catheter 2, are elastically stretched. As soon as this elastic stretching has been cancelled out, the closure part 5 with its conically configured contact part 7 returns to the position indicated with 7' in FIG. 4, in which the proximal end segment of the urine-emptying channel 3 is tightly sealed.

FIG. 5 shows an alternative form of the connection of the closure part 5 with the proximal end segment of the catheter 2, in an enlarged sectional view, similar to the sectional view shown in FIG. 3. According to FIG. 5, the urine-emptying channel 3 of the catheter 2 is closed off as in FIG. 3, in that the conically configured contact part 7 of the closure part 5 rests against the proximal end edge or border 8 of the urine-emptying channel 3 in question, forming a seal. The activation channel 4 is shown in the same state as in FIG. 3, whereby the proximal end segment, i.e. the closure wall 9 of the activation channel 4 lies opposite the activation surface 10 of the closure part 5, as in FIG. 3. In contrast to the conditions shown in FIG. 3, however, in FIG. 5 the closure part 5 is connected with the catheter 2 by means of a joint element 11, and by means of at least one elastic holder element 6. This means that the closure part 5 with its at least one elastic holder element 6 and the catheter 2 are configured to originally be coherent, and afterwards are brought into the position shown in FIG. 5. Here again, the at least one elastic holder element 6 is elastically connected with the catheter 2, such as by means of a glued connection, so that it permits lifting the closure element 5 from the catheter 2 in the longitudinal direction of the catheter.

FIG. 6 illustrates the conditions that are present if an activation fluid for activation of the closure part 5 and thereby for opening the urine-emptying channel 3 becomes effective in the activation channel 4, in an enlarged sectional view, proceeding from the enlarged sectional view shown in FIG. 3. In contrast to the conditions shown in FIG. 3, according to FIG. 6 the proximal closure wall 9 is pressed out of its original closure position shown in FIG. 3, in the axial direction of the activation channel 4 in question, as the result of an elevated activation pressure, by means of a dome or elevation 9'' of the activation channel 4, in such a manner that the urine-emptying channel 3 is opened for unhindered passage of urine. In this case, the conically configured contact part 7 with the contact surface of the closure part 5 is lifted off the end edge or border 8 at the proximal catheter end, as illustrated in FIG. 6.

Now that the conditions that are present at the proximal end segment of the catheter 2 shown in FIG. 1, i.e. those that are alternatively possible there, have been considered more closely, the conditions that are present in the region between the related proximal end segment of the catheter 2 and its distal end segment will be considered more closely.

In the region between the proximal and distal end segments, the catheter 2 has a balloon arrangement that can be filled with a fluid, to seal the bladder and to hold the catheter 2 in the bladder lumen, which arrangement consists, in the present case, of two balloons 12 and 13 disposed directly behind one another, which consist of silicone here, in each instance. The balloon 12 has an attachment part 14, 15 at its ends that lie in the longitudinal direction of the catheter, in each instance, with which the balloon 12 in question is attached to the catheter 2, such as by means of a biocompatible glued connection. In corresponding manner, the balloon 13 has attachment parts 16, 17 that lie at the front and at the back, in the longitudinal direction of the catheter 2, with which the balloon 13 in question is attached to the catheter 2, such as by means of a biocompatible glued connection. In FIG. 1, the two balloons 12, 13 are illustrated in the non-filled state, by means of solid lines; in FIG. 1, the filled state of the balloons 12, 13 is indicated with broken lines. Thus, the blow-up regions of the balloons 12, 13 are established between the attachment parts 14, 15 as well as 16, 17. At this point, it should be noted that the two balloons 12, 13, in deviation from the conditions explained above, do not have to be attached to the catheter 2 lying directly next to one another; instead, they can also be attached to the catheter 2 at a certain distance from one another, as is illustrated in FIG. 1 of DE 196 21 420 C2, for example.

Figure 7:
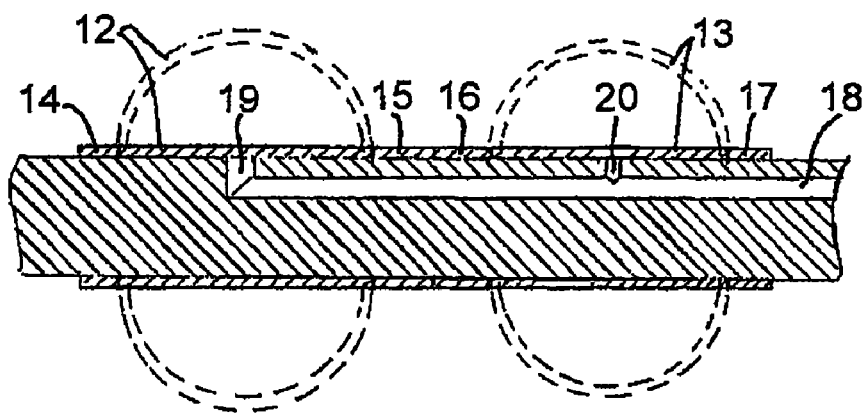
FIG. 7 illustrates a detail indicated in FIG. 1 as B, in an enlarged sectional view.

In order to illustrate the structure of the region with the balloons 12, 13 of the catheter 2 that was briefly discussed above in greater detail, reference is made to FIG. 7, in which the detail indicated with B in FIG. 1 is shown in an enlarged sectional view. In FIG. 7, the two balloons 12, 13 are shown with solid lines, also in the non-filled state; the filled state of the two balloons 12, 13 is shown with broken lines. In this connection, it is clearly evident from FIG. 7 that the blow-up region of the two balloons 12, 13 is established, in each instance, between their attachment points 14, 15 and 16, 17, respectively. Filling of the balloon 12 with a fluid, such as with water or a saline solution, for example, takes place by means of a filling channel 18 that runs along the catheter wall and is closed off at the distal end segment of the catheter 2, which channel has an exit opening 19 having a relatively large diameter, in the region of the balloon 12, in other words of the balloon lying at the proximal end of the catheter 2. The aforementioned fluid can be issued for the purpose of filling the balloon 12, by means of this exit opening 19, which can have the cross-section of the filling channel 18, for example. In order to be able to fill the second balloon 13 with the fluid, here the balloon 13 is connected with the filling channel 18 by means of a further exit opening 20. This exit opening 20 has a lesser cross-section than the exit opening 19 in the region of the balloon 12. By means of these measures, the fluid fills the filling region, i.e. blow-up region of the balloon 12 relatively quickly, and the balloon 13 fills more slowly than the balloon 12. The aforementioned channel 18 is now used not only for filling the balloons 12, 13 with a fluid, but also serves to guide away the fluid in question when the balloons 12, 13 are emptied.

At this point, it should also be noted that the two balloons 12, 13 could also be disposed essentially in series, in terms of fluid, in the case that the filling channel 18 were connected merely with the balloon 12, by means of a separate filling channel. In this case, as well, the balloon 12 would be filled first, and then the balloon 13.

Figure 8:
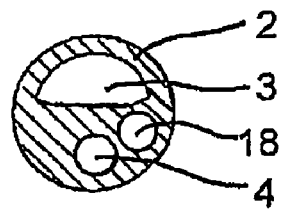
FIG. 8 illustrates an enlarged sectional view corresponding to the section line VIII-VIII drawn in FIG. 1.

FIG. 8 shows a sectional view along the sectional line VIII-VIII drawn in FIG. 1, in other words in the region between the two aforementioned balloons 12, 13. As is evident, the catheter 2 has the urine-emptying channel 3, the activation channel 4, and the channel 18 explained in connection with FIG. 7 in this region.

Coming back to FIG. 1, another detail C at the distal end region of the catheter 2, which is surrounded by a dot-dash line, will now be considered in greater detail. As indicated there, an activation balloon 23 is located at this distal catheter end region, which balloon also consists of silicone here, and is attached to the catheter 2 with attachment parts 24, 25, such as by means of a biocompatible glued connection. The detailed structure of the region that comprises the activation balloon 23 (Detail C), as established by a dot-dash circle in FIG. 1, is shown in an enlarged sectional view in FIG. 9.

Figure 9:
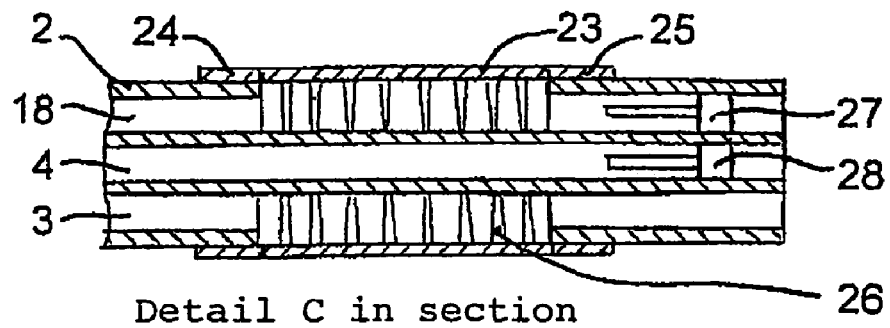
FIG. 9 illustrates a detail C indicated in FIG. 1 as C, in an enlarged sectional view.

As is evident from FIG. 9, the catheter 2 has the urine-emptying channel 3, now lying at the bottom and, lying above that, the activation channel 4 as well as the filling channel 18 at its distal end region. The activation channel 4 and the filling channel 18 can be closed off by means of valves 27 and 28, respectively, at the distal end of the catheter 2 that is shown on the right in FIG. 9. The urine-emptying channel 3, on the other hand, is open at the catheter end in question. The valves 27, 28 in question can be opened for the purpose of filling the activation channel 4 and the filling channel 18 with corresponding fluid, and they can furthermore be opened for the purpose of emptying the channels 4, 18 in question, but this will not be discussed in greater detail here.

The activation balloon 23, as is evident from FIG. 9, is attached to opposite regions of the catheter 2 with its attachment parts 24, 25. On its inside, it has a plurality of activation nubs 26, with which a certain mechanical pressure can be exerted on the wall of the activation channel 4. Since the entire device is configured in flexible manner, the wall of the activation channel 4 can be compressed by means of the aforementioned nubs 26 upon mechanical activation of the activation balloon 23, causing a corresponding pressure to be exerted on the activation fluid situated in the activation channel 4. This exertion of pressure is then utilized to open the valve provided at the proximal catheter end, as is illustrated in greater detail in an enlarged sectional view, according to FIG. 6, of the proximal catheter end in question. As was already explained in connection with FIG. 6, the closure wall 9 provided at the proximal end region of the activation channel 4 is brought out of its straight position as the consequence of pressure being exerted on the activation fluid in said channel, so that an elevation 9" forms, which acts against the activation surface, i.e. closure wall 10 of the closure part 5. In this way, the conically configured contact part 7 of the closure part 5 is brought away from the end edge, i.e. border 8 of the urine-emptying channel 3, so that the urine-emptying channel 3 is released for urine emptying. After pressure in the activation channel 4 has been relieved, the closure wall 9 of this activation channel 4 returns to the position shown in FIGS. 3 and 5, respectively, in which the urine-emptying channel 3 is closed again.

Now a Detail D in the activation channel 4, marked with a dot-dash circle in FIG. 6, will still be discussed. For this purpose, reference is particularly made to FIG. 10, which shows this Detail D in an enlarged sectional view. A separate valve 29 is disposed in the activation channel 4, close to the proximal catheter end, by means of which valve a separate pressure lumen is formed in the region of the activation channel 4 shown on the left, in each instance, in FIGS. 6 and 10, and when this lumen is filled with the activation fluid, by means of activation of the activation balloon 23 shown in FIGS. 1 and 6, the closure part 5 can be moved out of its sealing contact on the said urine-emptying channel 3 of the catheter 2. The valve 29 in question has a support part 30 connected with the interior of the activation channel 4, for example by means of a biocompatible glued connection, and a valve shaft 31 connected with this support part 30. Furthermore, the valve 29 has a lengthwise opening 32 that runs into the valve shaft 31 from the support part 30, and a crosswise hole 33 provided at the proximal end of said opening.

The region of the valve shaft 31 that contains the crosswise hole 33 is surrounded by a valve tube 34. Both the support part 30, like the valve shaft 31 and also the valve tube 34 can preferably consist of silicone. In its structure, the valve 29 that was considered above is therefore similar to a conventional bicycle tube valve.

Figure 10:
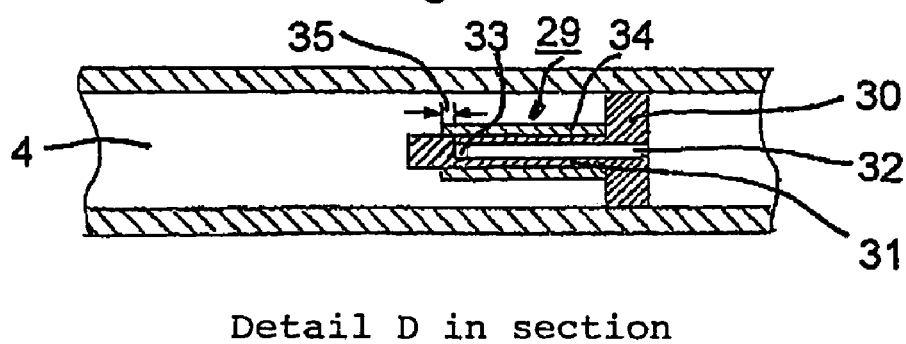
FIG. 10 illustrates a detail indicated in FIG. 6 as D, in an enlarged sectional view.

The intensity of the back-flow out of the pressure lumen of the activation channel 4, shown in the left in FIGS. 6 and 10, into the activation channel region shown on the right in the figures in question can be established by means of establishing the excess length of the valve tube 34 beyond the crosswise hole 33, indicated as 35 in FIG. 10. In this way, the valve 29 allows in-flow of the activation fluid into the region shown on the left in FIGS. 6 and 10, i.e. into the pressure lumen of the activation channel 4 that is situated there, at a first, relatively high velocity, and it permits back-flow of the activation fluid in question out of the region in question, i.e. the pressure lumen, at a significantly lesser second velocity, in comparison. By means of repeated activation of the activation balloon 23 at the distal catheter end—which practically represents pumpability—the region shown on the left in FIGS. 6 and 10 (pressure lumen) of the activation channel 4 can therefore be pumped up with the activation fluid, in a manner of speaking. Afterwards, the region in question (pressure lumen) of the activation channel 4 slowly empties again, in that the activation fluid escapes back into the region of the activation channel 4 shown on the right in FIGS. 6 and 10, through the region between valve shaft 31 and valve tube 34.

Figure 11:
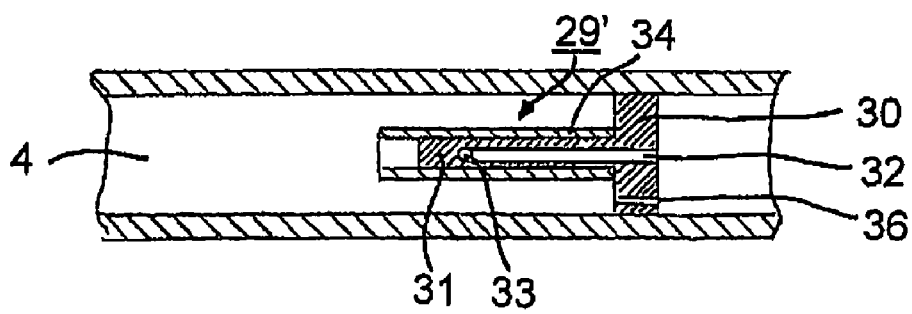
FIG. 11 illustrates an alternative implementation of the detail shown in FIG. 10, in an enlarged sectional view.

Now FIG. 11 will still be briefly discussed, which illustrates an alternative implementation of the valve 29 shown in FIG. 10. The valve shown in FIG. 11 is indicated as 29'; like the valve 29 shown in FIG. 10, it has a support part 30, a valve shaft 31, a lengthwise opening 32, and a crosswise hole 33 that is present at the proximal end of the latter, as well as a valve tube 34, which here, however, projects far beyond the valve shaft 31. All of the elements of the valve 29' can preferably consist of silicone. In contrast to the valve 29 shown in FIG. 10, the valve 29' has a back-flow opening 36 in its support part, which possesses a significantly smaller cross-section than the crosswise hole 33. If the crosswise hole possesses a diameter of 0.5 mm, for example, the diameter of the back-flow opening 36 lies in the micrometer range, such as in the range of 10 μm to 250 μm, for example.

REFERENCE SYMBOL LIST

| | |
|---|---|
| 1 | device |
| 2 | catheter |
| 3 | urine-emptying channel, emptying channel |
| 4 | activation channel |
| 5 | closure part |
| 6 | holder element |
| 7 | contact part |
| 7' | position of the contact part |
| 8 | end edge, border |
| 9 | closure wall |
| 9" | elevation, dome |
| 10 | activation surface |
| 11 | joint element |
| 12 | balloon |
| 13 | balloon |
| 14, 15 | attachment part |
| 16, 17 | attachment part |

-continued

| | |
|---|---|
| 18 | filling channel |
| 19 | exit opening |
| 20 | exit opening |
| 23 | activation balloon |
| 24, 25 | attachment part |
| 26 | activation nub |
| 27, 28 | valve |
| 29, 29' | valve |
| 30 | support part |
| 31 | valve shaft |
| 32 | lengthwise opening |
| 33 | crosswise hole |
| 34 | valve tube |
| 35 | excess length |
| 36 | backflow opening |
| A, B, C, D | detail |
| II-II | section |
| VIII-VIII | section |

The invention claimed is:

1. A device for treating bladder-emptying dysfunctions of a human, comprising:
a catheter that can be introduced into the urethra, said catheter having a urine-emptying channel and a balloon arrangement that can be filled with a fluid, to seal the bladder and to hold the catheter in a bladder lumen, said arrangement adapted to be filled with or emptied of said fluid by at least one channel that runs along a catheter wall and is sealed off at a distal end segment of the catheter;
an automatically closing valve accommodated in a proximal end segment of the catheter, wherein a length of the catheter is dimensioned so that its distal end lies within the urethra in the inserted state;
a hydraulic activation mechanism for opening the valve, said hydraulic activation mechanism being disposed in said proximal end segment;
an activation balloon disposed on the distal end segment of the catheter, said balloon being filled with activation fluid and connected with the activation mechanism by way of a connection channel, said activation balloon hydraulically impacting said activation mechanism by mechanical pressure on the activation balloon;
wherein the activation mechanism is formed by a closure part of the valve that is elastically connected with the proximal end segment of the catheter, so that the closure part seals off the catheter at the proximal end segment in a non-activated state of the activation balloon,
wherein the closure part can be moved out from sealing contact solely in response to a hydraulic impact from actuating the activation balloon by means of the effective hydraulic pressure built up at a closure wall of the connection channel at the proximal end segment; and
wherein the closure wall of the connection channel is opposite to an activation surface of the closure part and is pressed out of the connection channel in an axial direction by the hydraulic pressure so that the urine-emptying channel of the catheter is opened by the closure part for unhindered passage of urine.

2. The device according to claim 1, wherein the valve closure part has a conically shaped contact surface that makes it possible to seal off the urine-emptying channel of the catheter at an end edge at the proximal catheter end.

3. The device according to claim 1, wherein the closure part and the proximal end segment of the catheter are elastically connected with one another by holder elements.

4. The device according to claim 1, wherein the closure part is connected with the proximal end segment of the catheter by means of a joint element and at least one elastic holder element.

5. The device according to claim 4, wherein one end of each holder element is formed on the closure part or on the proximal end segment of the catheter, and is separately attached to the proximal end of the catheter or to the closure part, respectively, with its other end.

6. The device according to claim 5, wherein the other end of each holder element is separately attached to the proximal end segment of the catheter or to the closure part, respectively, by means of a glued connection.

7. The device according to claim 1, wherein the connection channel connected with the activation balloon contains a pressure lumen separated by a separate valve in a region of the proximal end segment of the catheter, and when said lumen is filled with the activation fluid by activation of the activation balloon, the closure part can be lifted up from its sealing contact on the urine-emptying channel of the catheter.

8. The device according to claim 7, wherein said separate valve allows in-flow of the activation fluid into the pressure lumen at a first, relatively high velocity, and permits backflow of the activation fluid from the pressure lumen at a significantly lower second velocity.

9. The device according to claim 8, wherein the separate valve, which separates the pressure lumen from the activation balloon, has a valve shaft that has a passage opening in the pressure lumen that is accessible from the activation balloon, which opening is surrounded by a valve tube.

10. The device according to claim 1, wherein the catheter and the closure part consist of silicone.

11. The device according to claim 1, wherein the balloon arrangement and the activation balloon consist of silicone.

12. The device according to claim 1, wherein the activation fluid is oil.

13. The device according to claim 12, wherein the oil is olive oil.

14. The device according to claim 3, wherein one end of each elastic holder element is formed on the closure part or on the proximal end segment of the catheter, and is separately attached to the proximal end of the catheter or to the closure part, respectively, with its other end.

* * * * *

UNITED STATES PATENT AND TRADEMARK OFFICE
CERTIFICATE OF CORRECTION

PATENT NO. : 7,766,901 B2
APPLICATION NO. : 10/585361
DATED : August 3, 2010
INVENTOR(S) : Mroncz et al.

Page 1 of 1

It is certified that error appears in the above-identified patent and that said Letters Patent is hereby corrected as shown below:

Title Page, item [75], Inventors: please change "Gabriele Wohnas" to correctly read:
--Gabriel Boehm-Wohnhas--.

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,766,901 B2
APPLICATION NO. : 10/585361
DATED : August 3, 2010
INVENTOR(S) : Mroncz et al.

It is certified that error appears in the above-identified patent and that said Letters Patent is hereby corrected as shown below:

Title Page, item [75], Inventors: please change "Gabriele Wohnas" to correctly read:
--Gabriele Boehm-Wohnhas--.

This certificate supersedes the Certificate of Correction issued September 14, 2010.

Signed and Sealed this

Ninth Day of November, 2010

David J. Kappos
*Director of the United States Patent and Trademark Office*